United States Patent [19]
Kuntz et al.

[11] Patent Number: 4,909,258
[45] Date of Patent: Mar. 20, 1990

[54] INTERNAL MAMMARY ARTERY (IMA) CATHETER

[75] Inventors: Richard E. Kuntz; Donald S. Baim, both of Newton, Mass.

[73] Assignee: The Beth Israel Hospital Association, Boston, Mass.

[21] Appl. No.: 229,927

[22] Filed: Aug. 8, 1988

[51] Int. Cl.$^4$ .............................................. A61B 6/00
[52] U.S. Cl. ................................... 128/658; 604/53; 604/102; 606/194
[58] Field of Search .................................. 128/656–658, 128/772, 343, 344, 348.1; 604/49–54, 95–105, 280, 281, 284

[56] References Cited

U.S. PATENT DOCUMENTS

| | | | |
|---|---|---|---|
| 4,137,906 | 2/1979 | Akiyama et al. | 604/102 X |
| 4,169,464 | 10/1979 | Obrez | 128/658 X |
| 4,456,000 | 6/1984 | Schjeldahl et al. | 604/53 |
| 4,601,706 | 7/1986 | Aillon | 604/102 X |
| 4,616,652 | 10/1986 | Simpson | 604/344 |
| 4,748,984 | 6/1988 | Patel | 604/658 |
| 4,763,654 | 8/1988 | Jang | 604/101 |
| 4,771,777 | 9/1988 | Horzewski et al. | 604/101 X |
| 4,781,677 | 11/1988 | Wilcox | 604/101 X |
| 4,790,331 | 12/1988 | Okada et al. | 604/53 X |

*Primary Examiner*—Dalton L. Truluck
*Attorney, Agent, or Firm*—Lorusso & Loud

[57] ABSTRACT

Apparatus for performing subselective arteriography or angioplasty on an internal mammary artery or graft which avoids dissection or stenosis of the internal mammary artery or graft. A catheter having a balloon and a proximal port delivers an angiographic dye or a device for treating vascular obstructions to the internal mammary artery or graft from a stable position within the subclavian artery.

Method for injecting angiographic dye into an internal mammary artery or graft. A catheter having and a balloon and a proximal port is inserted over a guide wire into a subclavian artery and inflated at a point distal to the junction of the subclavian artery and the internal mammary artery or graft. An angiographic dye is delivered through the proximal port and flows into the internal mammary artery or graft.

Method for cannulation of an internal mammary artery or graft which avoids dissection or stenosis of the internal mammary artery or graft. A catheter having a balloon and a proximal port is inserted over a guide wire into a subclavian artery and inflated at a point distal to the junction of the subclavian artery or internal mammary artery or graft. A device for treating vascular obstructions is advanced over a guide wire through the proximal port of the apparatus of the present invention and into the internal mammary artery or graft. Support for the device for treating vascular obstructions is provided by the catheter of the present invention, not by the internal mammary artery ostium.

13 Claims, 6 Drawing Sheets

INTERNAL MAMMARY ARTERY (IMA) CATHETER

BACKGROUND OF THE INVENTION

This invention relates to a method and apparatus to visualize an internal mammary artery (IMA), and more particularly, it relates to a method and apparatus to visualize and widen an internal mammary artery which has been used as a bypass graft without direct cannulation of the internal mammary artery.

Coronary bypass surgery involves shunting blood from the aorta to branches of the coronary arteries in order to increase blood flow beyond a local obstruction. The conduits used to divert or channel blood flow from the aorta are constructed from tissue taken from another part of a patient's body. The use of internal mammary artery (IMA) grafts for myocardial revascularization was introduced in 1969. (The term "graft" refers to the artery after bypass surgery as distinguished from "native vessel" or simply "IMA" which refers to the artery before the operation.) The recent resurgence in the advocacy of its use as the graft of choice is due to favorable long-term follow-up studies which demonstrate that this artery is resilient, adaptable, and durable.

Before and after bypass surgery, it is useful to examine the IMA and to repair it if necessary. Angiography is a desirable preoperative and follow-up procedure to bypass surgery because it enables a physician to visualize the integrity of the IMA using radiography after the injection of a radiopaque material into the vessel. Preoperative arteriography has also been advocated for assessing the utility of an IMA as a bypass graft. IMA arteriography allows comparison of the IMA caliber with the recipient coronary artery. See Singh, R., Cath. Card. Diag. 6:439–449 (1980). Reconstructive techniques are necessary to combat atherosclerosis, a natural, on-going process which results from a build-up of atherosclerotic and/or fibrocellular deposits within vessel walls. Balloon angioplasty, one such technique for treating stenosed vessels, may thus extend the useful life of a graft.

Unfortunately, the right and left internal mammary arteries are easily damaged using traditional angiography and angioplasty procedures. Guaranteed safe cannulation of the internal mammary artery during catheterization remains unrealized. Although dissection and occlusion of the IMA by the catheter tip is an uncommon consequence of catheterization, it is a serious complication. The mechanical sheer stress applied by the catheter to internal vascular walls may remove endothelium and expose subendothelial thrombogenic tissues. Consequently, platelets may adhere to these exposed surfaces and cause the release of platelet-derived growth factors resulting in possible smooth muscle proliferation and fibrous tissue deposition. See Pap, J., Cath. Card. Diag. 13:57–73. Even though native internal mammary arteries rarely develop atherosclerosis, surgical manipulation of the IMA during bypass surgery may lead to intimal damage and subsequent stenosis of these fragile vessels. The site of stenosis is usually the point where the IMA is anastomosed to a coronary artery. PCTA of the stenotic or occluded right and left IMA graft has been reported as a successful therapeutic modality for restoring normal flow to a grafted coronary artery without need to perform a repeat bypass operation. It involves placing a modified balloon catheter into the IMA via a vascular puncture in the femoral or brachial artery under local anesthesia. Inflation of the balloon within the narrowed section of the IMA widens the vessel lumen and restores normal blood flow. A guiding catheter (8–9 French) which is as large or larger than the ostium of the IMA, is placed so that its tip intubates the ostium of the IMA. Stabilization of the catheter is, in part, dependent upon this contact point. On the other hand, this intubation may cause mechanical stress and the aforementioned possible tissue damage.

Other methods of removing arterial obstructions involve purposeful selective intubation of a guiding catheter into the IMA to facilitate distal advancement of a balloon catheter, in particular, a dilatation catheter. Due to the angulated origin and smaller caliber of the IMA compared to the coronary arterial ostium, the IMA is probably more susceptible to dissection during selective arteriography. Reported cases of IMA dissection demonstrate the vulnerability of this artery to conventional selective catheterization techniques. (The term selective catheterization techniques encompasses selective arteriography and selective angioplasty. It refers to the standard practice of inserting a catheter into the subclavian artery and thence directly into the IMA.) In one case, selective catheterization caused ostial left IMA graft dissection resulting in a massive anteroseptal myocardial infarction. The dissection in that case was not recognized at the time of the catheterization. The recent resurgence of interest in using internal mammary arteries for coronary revascularization mandates more frequent IMA evaluations before and after contemplated coronary bypass surgery.

Certain anatomical features of the left and right internal mammary artery obviate simple selective catheterization and arteriography. A significant characteristic is the variable location of the junction of the internal mammary artery and the subclavian artery along the subclavian artery. In most cases, the junction of the IMA and the subclavian artery is on the inferior and slightly anterior surface of the subclavian artery, approximately 1–4 cm distal to the point where the subclavian artery originates. The standard method for catheterization of the left IMA from the femoral approach is the passage of a 0.035 J-tipped guide wire through a 7 or 8 French Right Judkins or preformed IMA catheter into the left subclavian artery. After the guide wire is successfully advanced past the presumed junction of the IMA and the subclavian artery, the catheter is then advanced over the guide wire to a distal position, usually near the origin of the axillary artery. (The axillary artery is a continuation of the subclavian artery.) The catheter is then withdrawn so that its acutely angled tip is dragged along an infero-anterior plane. Although occasional non-selective injections may identify the junction of the IMA and the subclavian artery, selective intubation usually requires careful catheter manipulation and withdrawals along different planes. This procedure may cause significant intimal damage and adds to the time required for arterial catheterization. Furthermore, once the ostium of the IMA is located, the difficulty associated with controlling the depth or alignment of the catheter tip within the IMA increases the risk of IMA trauma during contrast injection.

A special IMA catheter has been developed with acute primary and secondary 80 degree curves that can be used from the right brachial artery approach. See Singh, R., Cath. Card. Diag. 6:439 (1980). No guide wire is required. The catheter is advanced distally into the subclavian artery, and "some manipulation is necessary to engage the tip into the orifice [of the IMA]." Of 75 patients studied, this catheter was successful in selectively intubating the left IMA in 78% and non-selectively in another 16%. Citing "inherent technical problems" with the femoral approach, Dorros and Lewin proposed an ipsilateral brachial approach for placing a guiding catheter into the right and left IMA for angioplasty. See Dorros, G., and Lewin, R., Cath. Card. Diag. 12:341-46 (1986).

In a review of clinical and angiographic characteristics of IMA-coronary bypass grafts, 124 out of 217 patients were monitored with digital subtraction angiography (DSA) arteriography. See Rankin et al., J. Thorac. Card. Surg. 92:832846 (1986). DSA, a noninvasive form of arteriography which produces an image of inferior quality to selective angiography, was preferred over catheterization for many reasons, including technical catheterization difficulties and "improved visualization in patients with subclavian artery tortuosity or anomalous IMA origin."

A method of reliable subselective catheterization that does not involve direct cannulation but does allow highly specific access to the internal mammary artery for arteriography and angioplasty is needed in order to fully exploit this proven and widely used bypass graft.

SUMMARY OF THE INVENTION

In accordance with the present invention, it has been discovered that the left and right internal mammary arteries can be visualized and widened without resort to direct cannulation.

Accordingly, the present invention is an apparatus and an indirect method for injecting angiographic dye into an internal mammary artery or graft. A catheter having a balloon and a proximal port is inserted over a guide wire into a subclavian artery and the balloon is inflated at a point distal to the junction of the subclavian artery and the internal mammary artery or graft. An angiographic dye is delivered through the proximal port. The inflated balloon blocks dye run-off down the distal subclavian artery so that the dye subselectively flows through the internal mammary artery or graft.

The present invention is also an apparatus and indirect method for lumenal widening of an internal mammary artery or graft which avoids dissection of the artery. A catheter having a balloon and a proximal port is advanced over a guide wire into a subclavian artery such that the balloon is distal to the junction of the subclavian artery and the internal mammary artery or graft and the proximal port faces the internal mammary artery ostium. A guide wire is directed through the proximal port and into the internal mammary artery ostium. A device used for treating vascular obstructions, such as any one of those used in angioplasty or atherectomy, including balloon catheters, stents, and laser interventions, is advanced over a steerable guide wire into the internal mammary artery or graft.

It is therefore an object of the present invention to provide an apparatus and method for subselectively catheterizing an internal mammary artery or graft for arteriography without direct cannulation of the internal mammary artery or graft.

It is another object of the present invention to provide a method to subselectively catheterize an internal mammary artery for angioplasty without direct cannulation of the internal mammary artery.

DESCRIPTION OF THE PREFERRED EMBODIMENTS

At the outset, the invention is described in its broadest overall aspects with a more detailed description following. The broadest aspects of the invention involve inserting a catheter having a balloon and a proximal port into a subclavian artery, inflating the balloon at a point distal to the junction of the subclavian artery and the internal mammary artery or graft to obstruct the distal blood flow in the subclavian artery, and delivering angiographic dye through the proximal port. The inflated balloon blocks dye run-off down the distal subclavian artery so that dye subselectively flows through the internal mammary artery or graft. In this same position, a device used for treating vascular obstructions, such as any one of those used in angioplasty or atherectomy, including balloon catheters, stents and laser interventions, can be delivered over a steerable guide wire through the proximal port which faces the internal mammary artery ostium. In this manner, the device can be advanced into the internal mammary artery or graft such that support for the device is provided by the catheter and not by the internal mammary artery ostium.

Figure 1:
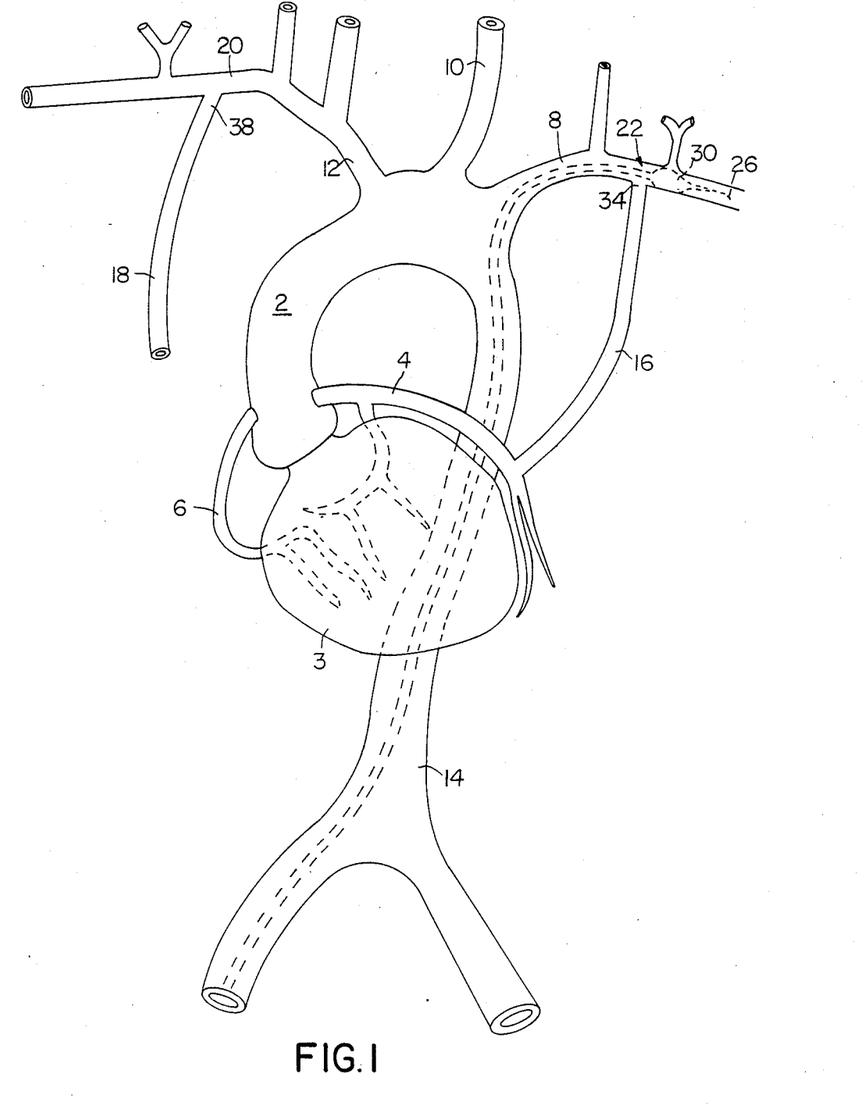
FIG. 1 is a diagram of the heart, the aorta and descending aorta, the left and right coronary arteries, the left and right internal mammary arteries, and the left and right subclavian arteries after surgical anastomosis of the left internal mammary to the left coronary artery, with the apparatus of the present invention positioned for treatment of the left internal mammary artery.

Referring to FIG. 1, the aorta 2 is the large arterial trunk that supplies oxygenated blood to the entire systemic circulation. Starting from the heart 3, the first branches off the aorta 2 are the left coronary artery 4 and the right coronary artery 6. Subsequent branches originating from the aorta 2 include the left subclavian artery 8, the left carotid 10, and the brachiocephalic artery 12. The descending aorta 14 delivers blood to the rest of the body. Because individual heart cells cannot exchange material with the blood being pumped through the chambers of the heart, blood flow through the coronary arteries is required to provide coronary circulation to the heart itself and maintain normal functioning of the heart. Blockage of a coronary artery results in transient dysfunction or even damage of heart muscle.

Coronary bypass surgery is a procedure which diverts blood from the aorta 2 to a branch of a coronary artery to increase blood flow beyond a local obstruction in a coronary artery. The diverted blood flows through a graft, a blood vessel from another part of the body which provides a conduit for the diverted blood flow. It is common to use veins from a patient's leg for this purpose. There has also been a resurgence in the use of internal mammary arteries as grafts.

The left internal mammary artery 16 is a branch of the left subclavian artery 8. The right internal mammary artery 18 is a branch of the right subclavian artery 20, which is itself a branch of the brachiocephalic artery 12. Both of the internal mammary arteries originate under a person's collar bone and supply blood to the chest wall muscles. Surgical anastomosis of the IMA for use as a graft involves dissecting the distal IMA free from the chest wall while the proximal portion remains attached to the subclavian artery. The distal portion is then attached to the selected, diseased coronary artery. The anatomical location of the internal mammary arteries makes them particularly desirable for use as grafts. Because only one end of the IMA must be surgically connected with a coronary artery, the incidence of stenosis, which usually afflicts the implanted regions of a graft, is immediately reduced. In addition, the diameter of internal mammary arteries is comparable to the diameter of coronary arteries. Furthermore, internal mammary artery grafts have a superior patency rate 10 years after surgery over that of saphenous vein grafts (95% versus 50% patency). See Loop, F. D., et al., 314 N.E.J.M. 1-6 (1986). Thus, an IMA graft is able to divert blood flow around an obstruction in the coronary artery efficiently.

Prior to using the IMA as a graft, its structural integrity may be confirmed via a procedure called arteriography. Arteriography, however, is not routinely performed due to the time, effort, and risk of IMA injury involved in current selective cannulation techniques. It is important to perform this procedure during post-operative catheterization of patients with recurrent angima to assure the continued patency of the graft. Other post-operative techniques may be used to extend the life of a graft by treating atheromatous plaque which can build up within the lumen of the graft over time. These techniques are known generally as angioplasty and atherectomy and include the use of balloon catheters, stents, and laser interventions. Angioplasty typically involves inflating a balloon catheter, called a dilatation catheter, such that pressure is applied to the blood vessel wall and the atheromatous plaque is fractured. Some atherectomy techniques include balloon catheters which utilize laser energy to heat the contents of the balloon and ultimately melt the atheromatous plaque. Still other laser interventions include the direct excision of atheromatous material.

The present invention obviates the need for selective intubation by the guiding catheter, dragging the catheter tip for IMA cannulation, and deep seating the catheter within the IMA, all procedures associated with current arteriography, angioplasty, and atherectomy techniques which may cause significant tension, torsion, and, ultimately, dissection and stenosis of the IMA. The lower risk of damage to the internal mammary artery using the present invention encourages the practice of examining the artery for damages prior to bypass surgery.

Figures 2, 3:
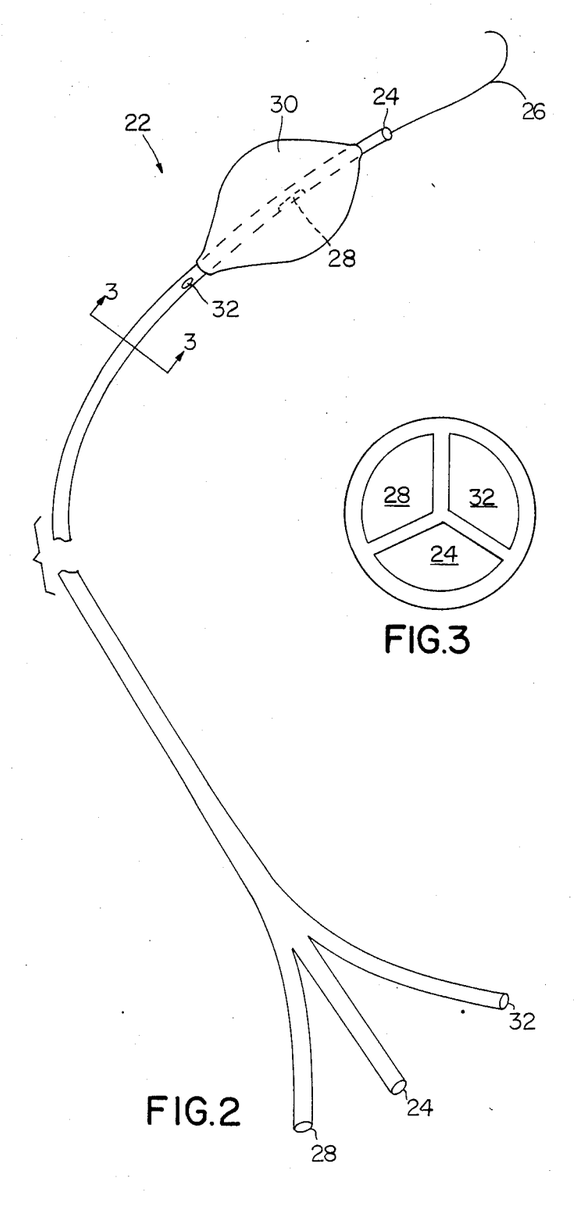
FIG. 2 is a plan view of the apparatus of the present invention.
FIG. 3 is a cross-sectional diagram of the apparatus of the present invention taken along the line 3—3.

Accordingly, the present invention makes use of the unique anatomical characteristics of internal mammary arteries that allow highly specific and nonselective catheterization for arteriography, angioplasty and atherectomy. Referring to FIGS. 2 and 3, the apparatus of the present invention is essentially a balloon catheter 22 having a distal port 24 for insertion over a guide wire 26, a balloon port 28 for inflation of a balloon 30, and a proximal port 32 for dye injection. The distal port 24 run the length of the catheter 22. The balloon port 28 extends from the most proximal end of the catheter 22 to point enclosed by the balloon 30. The proximal port 32 extends from the most proximal end of the catheter 22 to a point just proximal to the balloon 30.

The catheter 22 is a conventional catheter formed in the conventional manner and of a conventional material, with the exception that it has formed therein one additional lumen for dye injection and/or insertion of a guide wire and a device for treating vascular obstructions. The lumens are formed in the catheter 22 in a manner well-known in the art. The balloon 30 itself is a conventional balloon as employed in balloon flotation or balloon angioplasty. It is secured to the catheter 22 in the same manner utilized in securing balloons to the ends of such current catheters. The guide wire 26 is similar to the guide wire used to navigate catheters into position within an artery.

Figure 4:
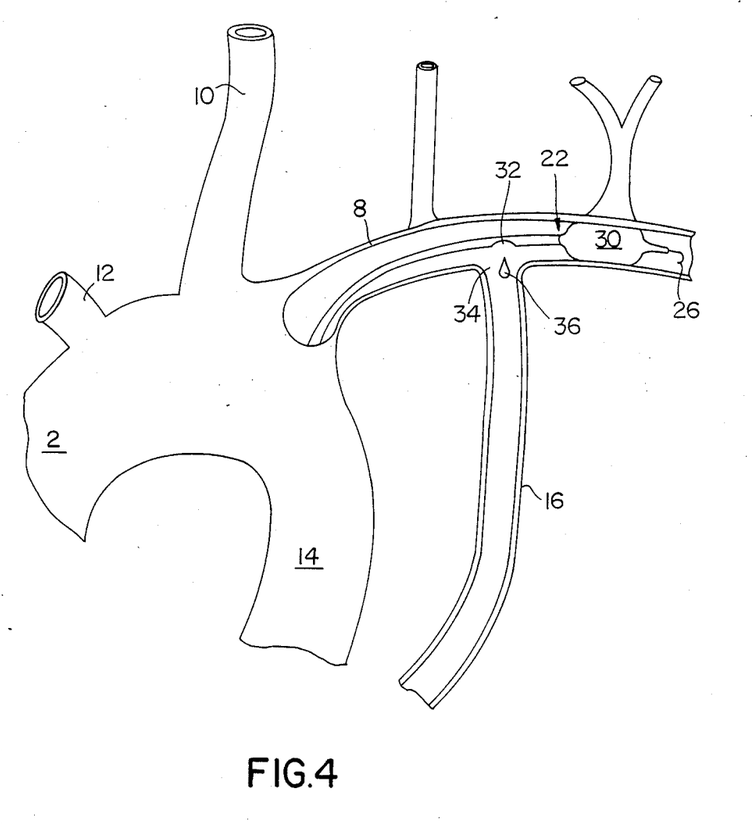
FIG. 4 is a cross-sectional diagram of the left subclavian artery and the left internal mammary artery showing the apparatus and method for visualizing a left internal mammary artery or graft.

Referring to FIG. 4, the procedure for visualizing the left IMA involves inserting a guide wire 26 up through the descending aorta 14 and into the left subclavian artery 8. The catheter 22 is positioned over the guide wire 26 such that the balloon 30 is located just distal to the left internal mammary artery ostium 34. Careful inflation of the balloon 30 obstructs distal blood flow to the axillary artery as well as stabilizes the catheter 22 within the left subclavian artery 8. Indeed, distal port pressure may be monitored through the guide wire to detect the instant at which the balloon occludes axillary flow during inflation. When properly placed, angiographic dye 36 injected through the proximal port 32 subselectively flows through the left internal mammary artery 16. The left internal mammary artery 16 can then be visualized using radiographic techniques.

Figure 5:
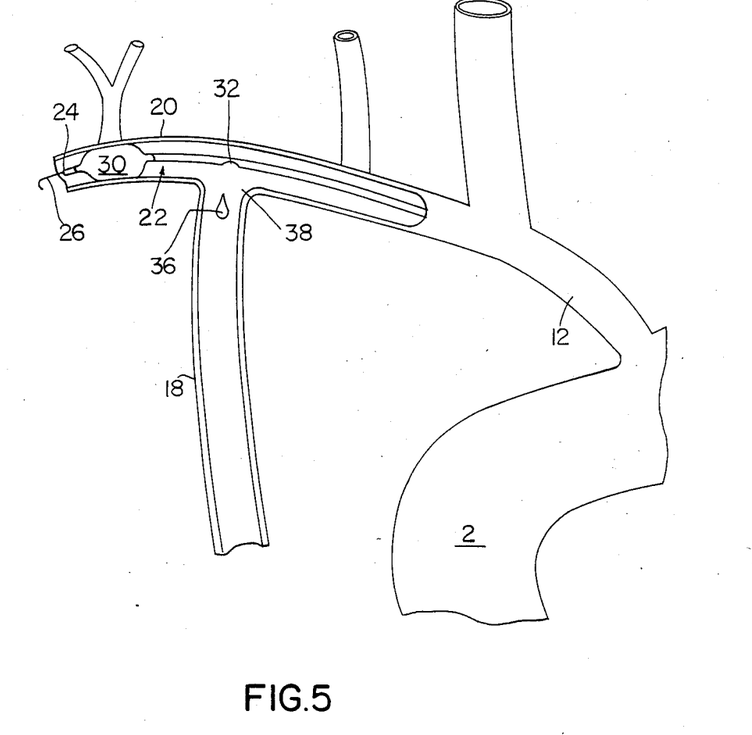
FIG. 5 is a cross-sectional diagram of the right subclavian artery and the right internal mammary artery showing the apparatus and method for visualizing a right internal mammary artery or graft.

The procedure for visualizing the right internal mammary artery is similar to the above procedure. See FIG. 5. The guide wire 26 is inserted up through the descending aorta 14, through the brachiocephalic artery 12 and into the right subclavian artery 20. The catheter 22 is positioned over the guide wire 26 such that the balloon 30 is located just distal to the right internal mammary ostium 38. Angiographic dye 36 injected through the proximal port 32 subselectively flows through the right internal mammary artery 18. At this point radiographic techniques are employed.

Figure 6:
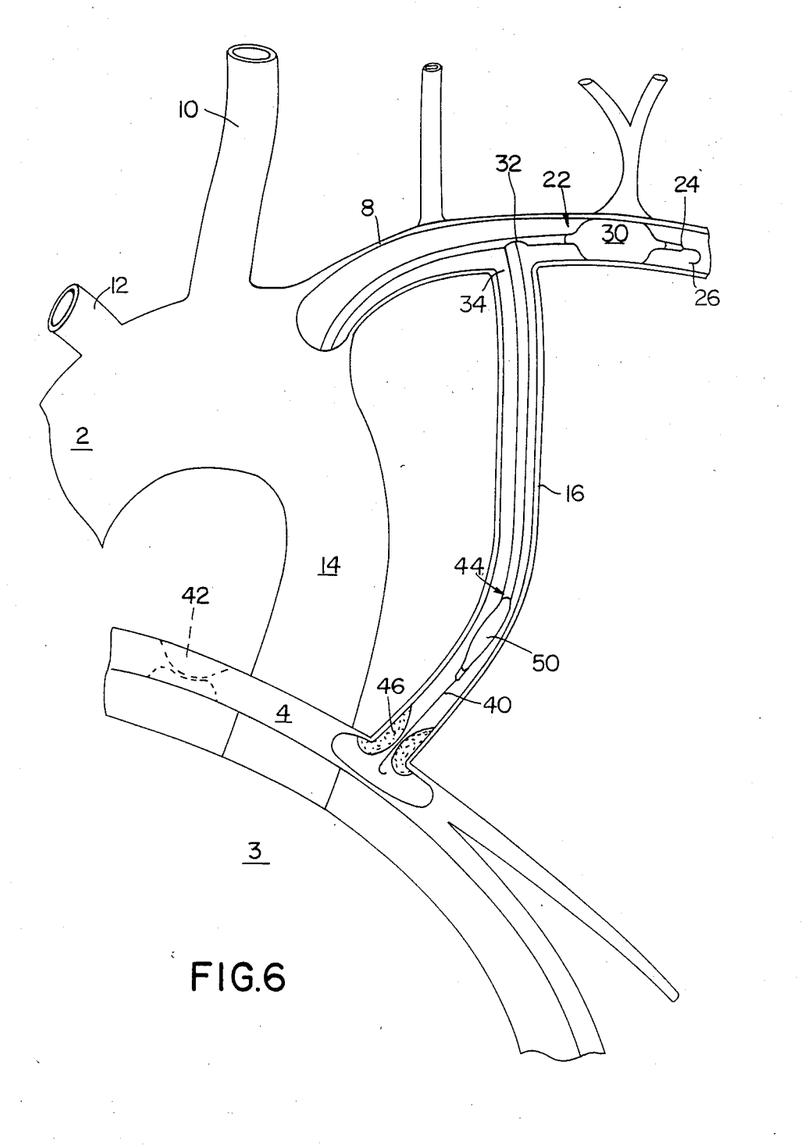
FIG. 6 is a cross-sectional diagram of the left subclavian artery and the left internal mammary artery graft anastomosed to the obstructed left coronary artery showing the apparatus and method for widening the lumen of a left internal mammary artery or graft.

Cannulation of the left IMA 16 is similarly performed using the device of the present invention. Referring to FIG. 6, the catheter 22 is advanced over the guide wire 26 and positioned within the left subclavian artery 8. The balloon 30 is inflated and stabilized at a point distal to the left internal mammary artery ostium 34. Then, via arteriographic opacification and fluoroscopic freeze framing, a steerable guide wire 40 is passed through the proximal port 32 of the catheter 22, through the left internal mammary artery ostium 34, and into the left IMA 16. (Note that the left IMA 16 is anastomosed to the occluded left coronary artery 4 beyond the site of occlusion on the left coronary artery 42.)

In the embodiment shown in FIG. 6, a balloon catheter 44 for treating vascular obstruction, which, for example, may be a dilatation catheter, is advanced over the secured guide wire 40 to the site of occlusion 46 within the left IMA 16. Once the balloon catheter 44 is properly positioned within the occluded area 46, a balloon 50 which is attached to the balloon catheter 44 is inflated. The support needed to perform angioplasty or atherectomy techniques within the left internal mammary artery 16 is provided by the larger more durable left subclavian artery 8 instead of the more fragile left internal mammary artery ostium 34 as in the current methods.

The above technique can also be performed on the right IMA 18. See FIG. 7. The catheter 22 is inserted over the guide wire 26 and positioned within the right subclavian artery 20 past the right IMA ostium 38. The balloon 30 is inflated and stabilized at a point distal to the right IMA ostium 38. Then, via arteriographic opacification and freeze framing, a steerable guide wire 40 is passed through the proximal port 32 of the catheter 22 through the right IMA ostium 38 and into the right IMA 18. In the embodiment shown in FIG. 7, a balloon catheter 44 for treating vascular obstructions, which, for example, may be a dilatation catheter, is advanced over the secured guide wire 40 to the site of occlusion 48 where the balloon 50 which is attached to the balloon catheter 44 is inflated. (Note that the right IMA 18 is anastomosed to the right coronary artery 6 beyond the site of occlusion 52 within the right coronary artery 6). The support needed to perform angioplasty within the right IMA 18 is provided by the larger more durable right subclavian artery 20 instead of the more fragile right IMA ostium 38.

Figure 7:
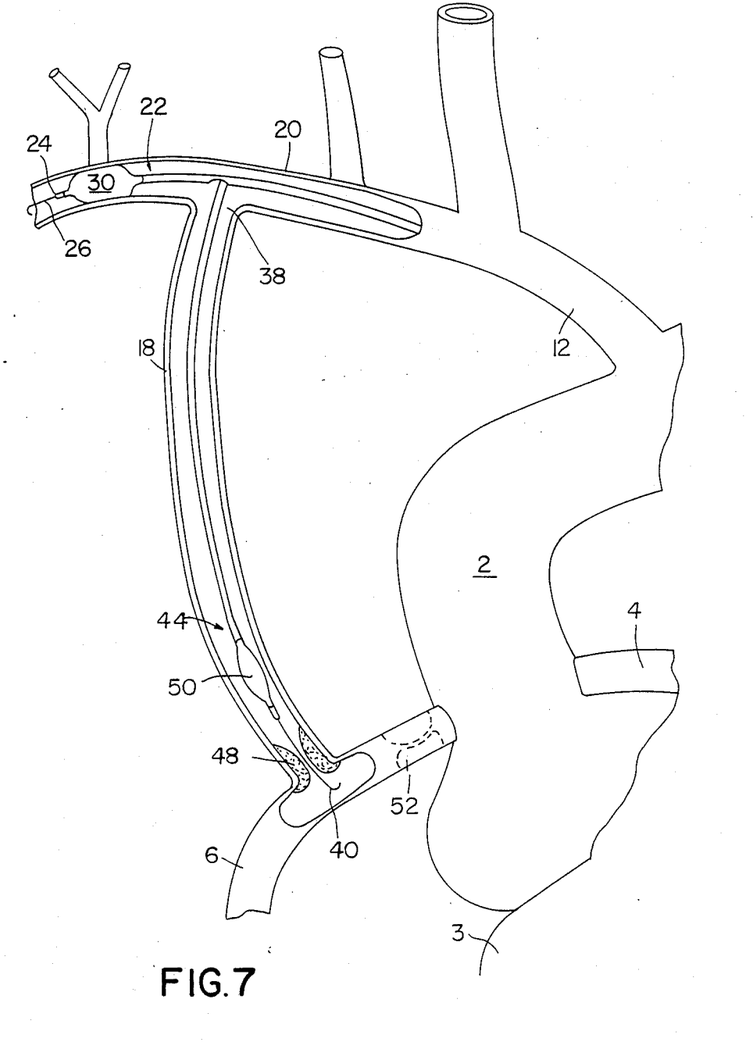
FIG. 7 is a cross-sectional diagram of the right subclavian artery and the right internal mammary artery graft anastomosed to the obstructed right coronary artery showing the apparatus and method for widening the lumen of a right internal mammary artery or graft.

In the embodiments shown in FIGS. 6 and 7, the balloon catheter 44 has a diameter of approximately 0.032–0.040 inch while the guide wire 32 over which it fits is approximately 0.014 inch in diameter. Thus, the lumen of the proximal port 32 must be at least 0.060 inch (commonly 0.080 inch) and lined with Teflon to permit easy advancement of the balloon catheter 44. The guiding catheter 22 must have a larger diameter (i.e. 8–9 French) for adequate lumen and wall thicknesses. Some extra clearance between the balloon catheter 44 and the inner wall of the guiding catheter 22 is also needed to allow contrast injection to visualize the artery during balloon advancement.

In addition to balloon catheters, other devices currently used in the treatment of vascular obstructions may be advanced through the proximal port 32 of the catheter 22. In this capacity, the catheter 22 functions as a protective sheath preventing the tension, the torsion, and the ultimate dissection and stenosis of the IMA which results from the direct cannulation of the IMA.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is not invention to exclude any equivalents thereof. Hence, it is recognized that various modifications are possible when within the scope of the present invention as claimed.

What is claimed is:

1. A method for visualizing an internal mammary artery which avoids direct cannulation of the internal mammary artery comprising the following steps:
   (a) inserting a guide wire up through the descending aorta and into the subclavian artery beyond the junction of the subclavian artery and the internal mammary artery;
   (b) advancing a catheter having a balloon and a proximal port each with a separate lumen that begins at the proximal end of the catheter over said guide wire into the subclavian artery such that the balloon is distal to the junction of the subclavian artery and the internal mammary artery and the proximal port is positioned directly above the junction of the subclavian artery and the internal mammary artery;
   (c) inflating said balloon to obstruct distal blood flow to an axillary artery and to stabilize said catheter;
   (d) injecting an angiographic dye through said proximal port into said internal mammary artery; and
   (e) visualizing the angiographic dye using radiography.

2. The method of claim 1 wherein in step (a) the guide wire is inserted into the left subclavian artery beyond the junction of the internal mammary artery with the left subclavian artery and in step (b) the catheter is advanced over the guide wire into the left subclavian artery such that the balloon is distal to the junction of the internal mammary artery and the left subclavian artery and the proximal port is positioned directly above the junction of the internal mammary artery and the left subclavian artery.

3. The method of claim 1 wherein in step (a) the guide wire is inserted into the right subclavian artery beyond the junction of the internal mammary artery with the right subclavian artery and in step (b) the catheter is advanced over the guide wire into the right subclavian artery such that the balloon is distal to the junction of the internal mammary artery and the right subclavian artery and the proximal port is positioned directly above the junction of the internal mammary artery and the right subclavian artery.

4. A method for visualizing an internal mammary artery graft which avoids direct cannulation of the internal mammary artery graft comprising the following steps:
   (a) inserting a guide wire up through the descending aorta and into the subclavian artery beyond the junction of the subclavian artery and the internal mammary artery graft;
   (b) advancing a catheter having a balloon and a proximal port each with a separate lumen that begins at the proximal end of the catheter over said guide wire into the subclavian artery such that the balloon is distal to the junction of the subclavian artery and the internal mammary artery graft and the proximal port is positioned directly above the junction of the subclavian artery and the internal mammary artery graft;
   (c) inflating said balloon to obstruct distal blood flow to an axillary artery and to stabilize said catheter;
   (d) injecting an angiographic dye through said proximal port into said internal mammary artery graft; and
   (e) visualizing the angiographic dye using radiography.

5. The method of claim 1 wherein in step (a) the guide wire is inserted into the left subclavian artery beyond the junction of the internal mammary artery graft with the left subclavian artery and in step (b) the catheter is advanced over the guide wire into the left subclavian artery such that the balloon is distal to the junction of the internal mammary artery graft and the left subclavian artery and the proximal port is positioned directly above the junction of the internal mammary artery graft and the left subclavian artery.

6. The method of claim 1 wherein in step (a) the guide wire is inserted into the right subclavian artery beyond the junction of the internal mammary artery graft with the right subclavian artery and in step (b) the catheter is advanced over the guide wire into the right subclavian artery such that the balloon is distal to the junction of the internal mammary artery graft and the right subclavian artery and the proximal port is positioned directly above the junction of the internal mammary artery graft and the right subclavian artery.

7. A method for widening an internal mammary artery which avoids direct cannulation of the internal mammary artery comprising the following steps:
  (a) inserting a guide wire through the descending aorta and into the subclavian artery beyond the junction of the subclavian artery and the internal mammary artery;
  (b) advancing a catheter having a balloon and a proximal port over said guide wire into the subclavian artery such that the balloon is distal to the junction of the subclavian artery and the internal mammary artery and the proximal port is positioned directly above the junction of the subclavian artery and the internal mammary artery;
  (c) inflating said balloon to obstruct distal blood flow to an axillary artery and to stabilize said catheter;
  (d) inserting a guide wire through said proximal port and into the internal mammary artery; and
  (e) advancing a means for treating vascular obstructions over said guide wire;

wherein said catheter is supported within said subclavian artery such that intimal damage to the internal mammary artery caused by said means for treating vascular obstructions is reduced.

8. The method of claim 7 wherein in step (a) the guide wire is inserted into the left subclavian artery beyond the junction of the internal mammary artery with the left subclavian artery and in step (b) the catheter is advanced over the guide wire into the left subclavian artery such that the balloon is distal to the junction of the internal mammary artery and the left subclavian artery and the proximal port is positioned directly above the junction of the internal mammary artery and the left subclavian artery.

9. The method of claim 7 wherein in step (a) the guide wire is inserted into the right subclavian artery beyond the junction of the internal mammary artery with the right subclavian artery and in step (b) the catheter is advanced over the guide wire into the right subclavian artery such that the balloon is distal to the junction of the internal mammary artery and the right subclavian artery and the proximal port is positioned directly above the junction of the internal mammary artery and the right subclavian artery.

10. A method for widening an internal mammary artery graft which avoids direct cannulation of the internal mammary artery graft comprising the following steps:
  (a) inserting a guide wire through the descending aorta and into the subclavian artery beyond the junction of the subclavian artery and the internal mammary artery graft;
  (b) advancing a catheter having a balloon and a proximal port over said guide wire into the subclavian artery such that the balloon is distal to the junction of the subclavian artery and the internal mammary artery graft and the proximal port is positioned directly above the junction of the subclavian artery and the internal mammary artery graft;
  (c) inflating said balloon to obstruct distal blood flow to an axillary artery and to stabilize said catheter;
  (d) inserting a guide wire through said proximal port and into the internal mammary artery graft; and
  (e) advancing a means for treating vascular obstructions over said guide wire;

wherein said catheter is supported within said subclavian artery such that intimal damage to the internal mammary artery graft caused by said means for treating vascular obstructions is reduced.

11. The method of claim 7 wherein in step (a) the guide wire is inserted into the left subclavian artery beyond the junction of the internal mammary artery graft with the left subclavian artery and in step (b) the catheter is advanced over the guide wire into the left subclavian artery such that the balloon is distal to the junction of the internal mammary artery graft and the left subclavian artery and the proximal port is positioned directly above the junction of the internal mammary artery graft and the left subclavian artery.

12. The method of claim 7 wherein in step (a) the guide wire is inserted into the right subclavian artery beyond the junction of the internal mammary artery graft with the right subclavian artery and in step (b) the catheter is advanced over the guide wire into the right subclavian artery such that the balloon is distal to the junction of the internal mammary artery graft and the right subclavian artery and the proximal port is positioned directly above the junction of the internal mammary artery graft and the right subclavian artery.

13. The method of claim 7 wherein in step (e) a balloon catheter is advanced over said guide wire.

* * * * *